US009910429B2

(12) United States Patent
Berg et al.

(10) Patent No.: US 9,910,429 B2
(45) Date of Patent: Mar. 6, 2018

(54) SYSTEMS AND METHODS FOR ADJUSTING TARGET MANUFACTURING PARAMETERS ON AN ABSORBENT PRODUCT CONVERTING LINE

(71) Applicant: The Procter & Gamble Company, Cincinnati, OH (US)

(72) Inventors: Eric Christopher Berg, Mainville, OH (US); Louis J. Cedrone, Mason, OH (US); Jeffrey Michael Kent, Lebanon, OH (US); Helen Louise Von Den Steinen, Bad Soden am Taunus (DE); William Lawrence Lightcap, Indian Hill, OH (US); Daniel Royce, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 734 days.

(21) Appl. No.: 14/474,554

(22) Filed: Sep. 2, 2014

(65) Prior Publication Data
US 2015/0066187 A1 Mar. 5, 2015

Related U.S. Application Data

(60) Provisional application No. 61/872,885, filed on Sep. 3, 2013.

(51) Int. Cl.
*G05B 19/418* (2006.01)
*A61F 13/15* (2006.01)
(52) U.S. Cl.
CPC .. *G05B 19/41875* (2013.01); *A61F 13/15772* (2013.01); *A61F 13/15804* (2013.01);
(Continued)

(58) Field of Classification Search
None
See application file for complete search history.

(56) References Cited

U.S. PATENT DOCUMENTS 4,854,984 A 8/1989 Ball et al.
6,248,195 B1 6/2001 Schmitz
(Continued)

OTHER PUBLICATIONS

PCT/US2014/053849 PCT International Search Report, dated Apr. 8, 2015, 13 pages.

*Primary Examiner* — Tuan Dao
(74) *Attorney, Agent, or Firm* — Charles R. Matson

(57) ABSTRACT

Systems and processes herein may be configured to correlate manufacturing parameters and performance feedback parameters with individual absorbent articles manufactured by a converting apparatus. Embodiments of the systems herein may include inspection sensors configured to inspect substrates and/or component parts advancing along the converting line and communicate inspection parameters to a controller and historian. The systems may also include process sensors configured to monitor equipment on the converting line and communicate process parameters to the controller and historian. The systems herein may also be adapted to receive performance feedback parameters based on the packaged absorbent articles. The systems may correlate inspection parameters, process parameters, and/or performance feedback parameters with individual absorbent articles produced on the converting line. The controller may also be configured to perform various functions based on the performance feedback parameters.

20 Claims, 10 Drawing Sheets

(52) U.S. Cl.
CPC .............. *G05B 2219/32182* (2013.01); *G05B 2219/32196* (2013.01)

(56) References Cited

U.S. PATENT DOCUMENTS

| | | | |
|---|---|---|---|
| 6,372,951 B1 * | 4/2002 | Ter-Ovanesyan .. | A61B 5/04884 600/373 |
| 6,450,321 B1 | 9/2002 | Blumenthal et al. | |
| 6,705,453 B2 | 3/2004 | Blumenthal et al. | |
| 6,801,828 B2 | 10/2004 | Popp et al. | |
| 6,811,019 B2 | 11/2004 | Christian et al. | |
| 6,814,217 B2 | 11/2004 | Blumenthal et al. | |
| 6,829,516 B2 | 12/2004 | Popp et al. | |
| 6,845,278 B2 | 1/2005 | Popp et al. | |
| 7,032,816 B2 | 4/2006 | Markham et al. | |
| 7,035,877 B2 | 4/2006 | Markham et al. | |
| 7,156,311 B2 | 1/2007 | Attia et al. | |
| 7,162,319 B2 | 1/2007 | Popp et al. | |
| 7,242,816 B2 | 7/2007 | Attia et al. | |
| 7,245,780 B2 | 7/2007 | Attia et al. | |
| 7,287,696 B2 | 10/2007 | Attia et al. | |
| 7,309,015 B2 | 12/2007 | Frantz et al. | |
| 7,357,298 B2 | 4/2008 | Pokorny et al. | |
| 7,380,213 B2 | 5/2008 | Pokorny et al. | |
| 7,387,250 B2 | 6/2008 | Muni | |
| 7,401,728 B2 | 7/2008 | Markham et al. | |
| 7,882,438 B2 | 2/2011 | Markham et al. | |
| 8,145,338 B2 | 3/2012 | Kent et al. | |
| 8,145,343 B2 | 3/2012 | DeBruler et al. | |
| 8,145,344 B2 | 3/2012 | DeBruler et al. | |
| 8,150,163 B2 | 4/2012 | Kruppa | |
| 8,376,232 B2 | 2/2013 | Eckstein et al. | |
| 8,799,113 B2 | 8/2014 | Markham et al. | |
| 2003/0091969 A1 * | 5/2003 | Supinski ................ | G06Q 30/02 434/273 |
| 2005/0043841 A1 | 2/2005 | Popp et al. | |
| 2006/0290517 A1 * | 12/2006 | Cohen .................... | A61B 5/038 340/573.1 |
| 2007/0142798 A1 | 6/2007 | Goodiander et al. | |
| 2007/0142806 A1 | 6/2007 | Roe et al. | |
| 2007/0203604 A1 | 8/2007 | Chiu et al. | |
| 2007/0287983 A1 | 12/2007 | Lodge et al. | |
| 2008/0132865 A1 | 6/2008 | Li et al. | |
| 2010/0305740 A1 * | 12/2010 | Kent ................ | A61F 13/15772 700/110 |
| 2011/0247199 A1 | 10/2011 | LaVon et al. | |
| 2012/0173249 A1 | 7/2012 | Popp et al. | |
| 2013/0072887 A1 * | 3/2013 | LaVon .................... | A61F 13/49 604/368 |
| 2013/0270728 A1 | 10/2013 | Denes et al. | |

* cited by examiner

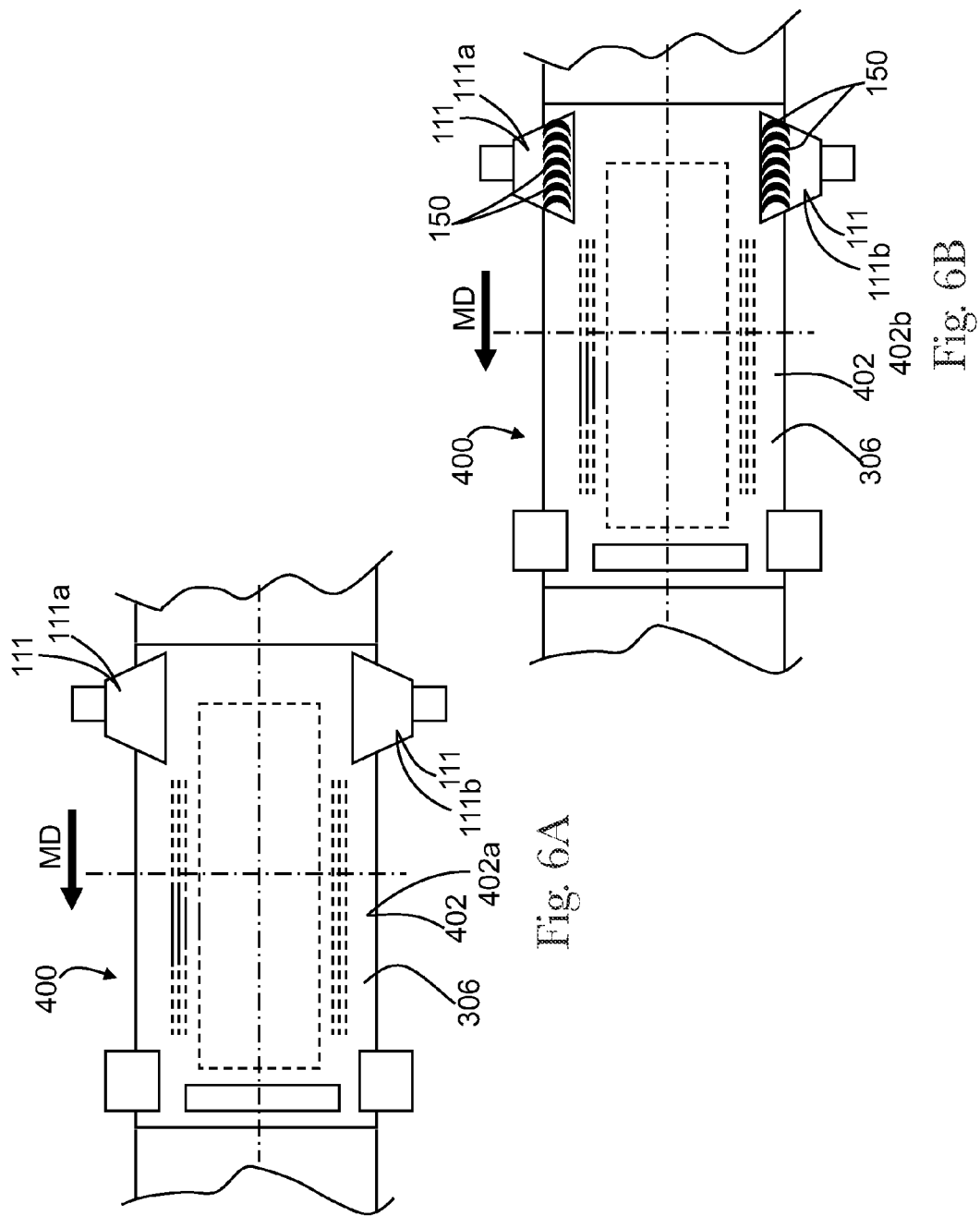

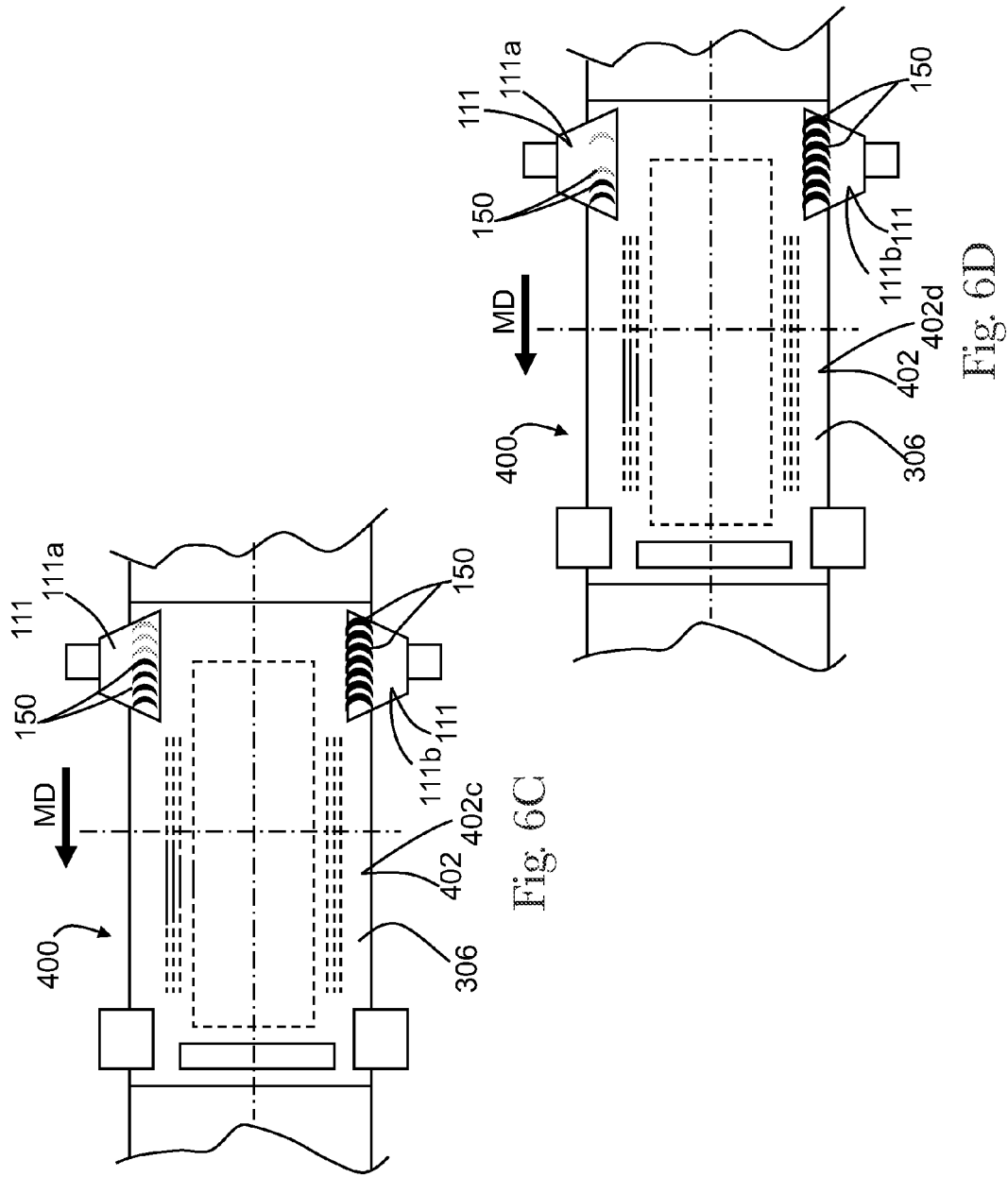

SYSTEMS AND METHODS FOR ADJUSTING TARGET MANUFACTURING PARAMETERS ON AN ABSORBENT PRODUCT CONVERTING LINE

CROSS REFERENCE TO RELATED APPLICATION

This application claims the benefit of U.S. Provisional Application No. 61/872,885 filed on Sep. 3, 2013, which is incorporated herein by reference.

FIELD OF THE INVENTION

The present disclosure relates to systems and methods for manufacturing disposable absorbent articles, and more particularly, systems and methods for adjusting target manufacturing parameters on a converting apparatus based on performance feedback parameters and manufacturing parameters that are correlated with individual absorbent articles manufactured by the converting apparatus.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

For quality control purposes, absorbent article converting lines may utilize various types of sensor technology to inspect the webs and discrete components added to the webs along the converting line as absorbent articles are constructed. Example sensor technology may include vision systems, photoelectric sensors, proximity sensors, laser or sonic distance detectors, and the like. Product inspection data from the sensors may be communicated to a controller in various ways. In turn, the controller may be programmed to receive product inspection data, and in turn, make adjustments to manufacturing process. In some instances, the controller may reject defective diapers based on the product inspection data after the final knife cut at the end of the converting line.

In addition, absorbent article converting lines may utilize various types of process sensor technology to monitor the performance of various types of assembly equipment used on the converting line. Example process sensor technology may include speed sensors, linear or radial position sensors, temperature, pressure or vacuum sensors, vision systems, proximity sensors, and the like. Process data from the process sensors may be communicated to a controller in various ways. In turn, the controller may be programmed to receive process data, and in turn, make adjustments to manufacturing process and/or communicate potential problems associated with assembly equipment to converting line operators. In some instances, based on the process data, the controller may automatically shutdown the converting line.

In further efforts to improve and control quality of manufactured absorbent articles, manufacturers may conduct extensive product testing and/or consumer research on various aspects of absorbent articles. Product performance data obtained from such product testing, in turn, may be used as a tool by manufacturers to make future converting equipment and/or processing adjustments.

Consequently, it would be beneficial to provide a system that is capable of precisely correlating product inspection data, process data, and product performance data with each other and/or with corresponding absorbent articles from where such data is obtained. However, there are challenges associated with precise correlation of such data. For example, the controller may not be able to correlate product inspection data with exact locations in the web and corresponding diapers with a very large degree of accuracy due to slow sensor response, data transportation delays and control loop execution times. For example, the sensor and control technologies may work asynchronously of each other, thus creating control system accuracy challenges, which may be exacerbated at the high speed production rates of some absorbent article processes.

Further, product inspection data and process data is traditionally recorded and correlated to the time at which the data was acquired. As such, an event that happens upstream in the process and causes a second event downstream would be recorded with different time-stamps and cannot be easily correlated without extensive data processing and detailed knowledge of the process conditions at the time.

Finally, when products are inspected away from the manufacturing process, such as in a quality assurance lab, the data may be stored with a time-stamp generated at the moment that the data is posted to the database, rather than the time-stamp at which the product was produced. The same time-stamp issue is present for product performance data, which is sometimes obtained at a significantly different time than the time at which the product was produced. For these same reasons, the controller may not be able to precisely correlate obtained process data and/or product performance data with inspection data and/or manufactured absorbent articles.

SUMMARY OF THE INVENTION

The present disclosure relates to systems and processes that may be configured to correlate manufacturing parameters and performance feedback parameters with individual absorbent articles manufactured by a converting apparatus. Embodiments of the systems herein may include inspection sensors configured to inspect substrates and/or component parts advancing along the converting line and communicate inspection parameters to a controller and historian. The systems may also include process sensors configured to monitor equipment on the converting line and communicate process parameters to the controller and historian. The systems herein may also be adapted to receive performance feedback parameters based on the packaged absorbent articles. The systems may correlate inspection parameters, process parameters, and/or performance feedback parameters with individual absorbent articles produced on the converting line. The controller may also be configured to perform various functions based on the performance feedback parameters.

In one form, a method for manufacture absorbent products includes the steps of: providing a communication network; connecting a first sensor with the communication network; connecting a second sensor with the communication network; connecting a controller with the communication network; advancing a substrate in a machine direction through a converting apparatus; virtually segmenting the substrate into a plurality of virtual products along the machine direction; virtually dividing the virtual products into a plurality of virtual segments along the machine direction; sequentially adding component parts to the substrate; inspecting the substrate and component parts with the first sensor; communicating inspection parameters from the first sensor to the controller; comparing the inspection parameter with a target inspection parameter; inspecting a process with the second sensor; communicating process parameters from the second sensor to the controller; comparing the process parameters with a target process parameter; cutting the substrate with component parts added thereto into discrete absorbent articles; packaging the discrete absorbent articles; receiving performance feedback parameters based on the packaged absorbent articles; correlating at least one inspection parameter with a selected packaged absorbent article; correlating at least one process parameter with the selected packaged absorbent article; correlating at least one performance feedback parameter with the selected packaged absorbent article; and adjusting at least one target inspection parameter or at least one the target process parameter based on the performance feedback parameter.

In another form, a method for manufacture absorbent products includes the steps of: providing a communication network; connecting a first sensor with the communication network; connecting a second sensor with the communication network; connecting a controller with the communication network; advancing a substrate in a machine direction through a converting apparatus; virtually segmenting the substrate into a plurality of virtual products along the machine direction; virtually dividing the virtual products into a plurality of virtual segments along the machine direction; sequentially adding component parts to the substrate; inspecting the substrate and component parts with the first sensor; communicating inspection parameters and time-stamps from the first sensor to the controller; inspecting a process with the second sensor; communicating process parameters and time-stamps from the second sensor to the controller; normalizing time-stamps for inspection parameters to a reference location or product; normalizing time-stamps for process parameters to a reference location or product; cutting the substrate with component parts added thereto into discrete absorbent articles; packaging the discrete absorbent articles; receiving performance feedback parameters based on the packaged absorbent articles; determining and normalizing time-stamps for performance feedback parameters to a reference location or product; correlating at least one inspection parameter with a selected packaged absorbent article; correlating at least one process parameter with the selected packaged absorbent article; correlating at least one performance feedback parameter with the selected packaged absorbent article; and storing inspection parameters, process parameters, and product performance parameters in a historian.

BRIEF DESCRIPTION OF THE DRAWINGS

FIG. 6A is view of the base substrate from FIG. 5A taken along line 6A-6A.

FIG. 6B is view of the base substrate from FIG. 5B taken along line 6B-6B.

FIG. 6C is view of the base substrate from FIG. 5C taken along line 6C-6C.

FIG. 6D is view of the base substrate from FIG. 5D taken along line 6D-6D.

DETAILED DESCRIPTION OF THE INVENTION

Figure 1:
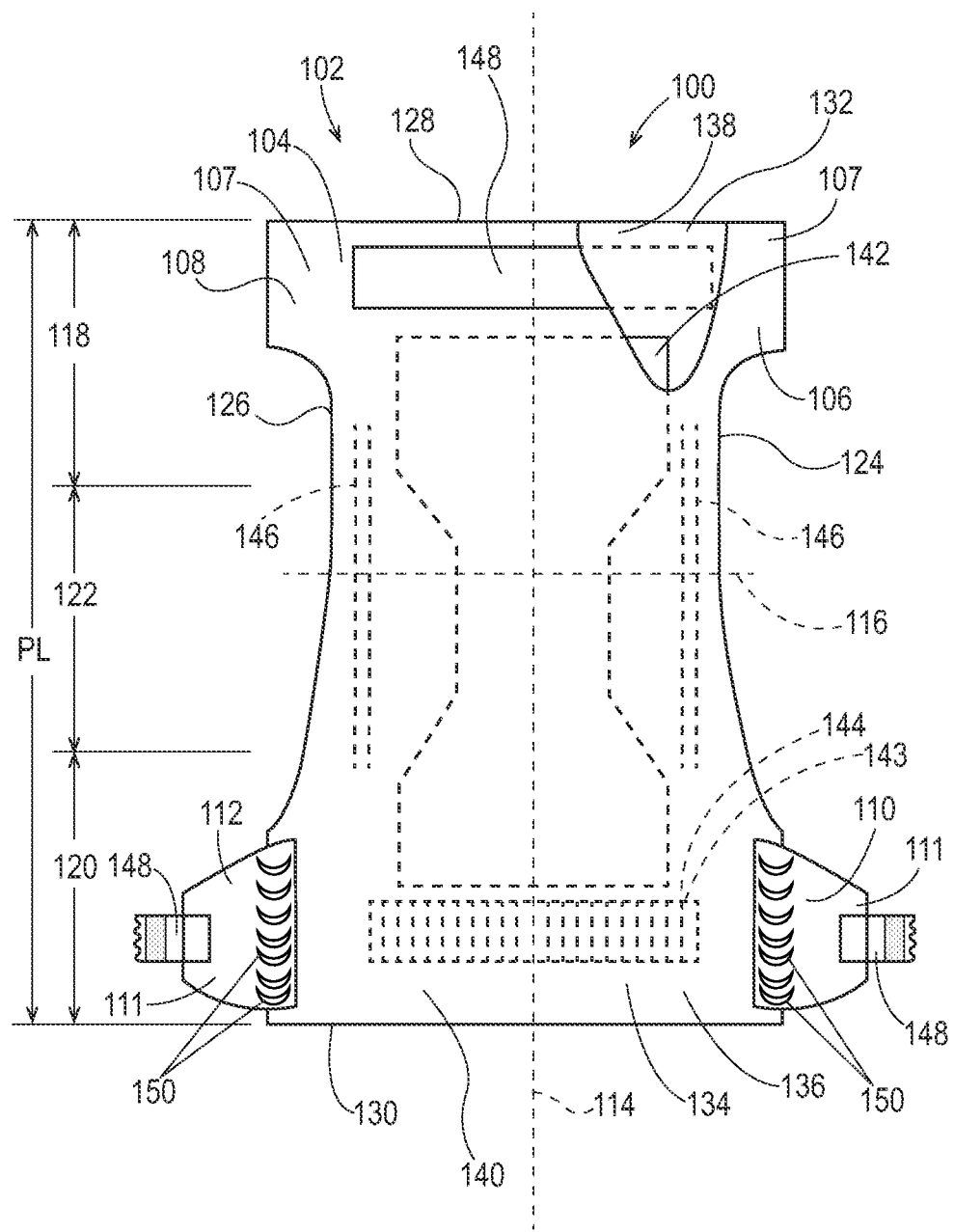
FIG. 1 is a top plan view of a disposable absorbent article that may include one or more substrates and/or components manufactured in accordance with the present disclosure.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from an end edge, such as a waist edge to a longitudinally opposing end edge, or waist edge, of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a defined woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The terms "normalized time" and "normalized timestamp" are used herein to refer to a time representing the instant that a product was present at a certain reference position.

The present disclosure relates to systems and processes manufacturing absorbent articles. More particularly, the systems and processes herein may be configured with a historian to maintain a database of process data and product inspection data, and/or a controller to correlate manufacturing parameters and performance feedback parameters with individual absorbent articles manufactured by a converting apparatus. In turn, the controller may adjust target manufacturing parameters on the converting apparatus based on the correlated manufacturing and performance feedback parameters. As discussed below, embodiments of the systems herein may include a converting line adapted to produce absorbent articles, wherein the converting line includes inspection sensors, process sensors, a controller, and a historian connected with a communication network. Inspection sensors may be configured to inspect substrates and/or component parts advancing along the converting line and communicate inspection parameters to the controller and historian. Process sensors may be configured to monitor equipment on the converting line and communicate process parameters to the controller and historian. The systems herein may also be adapted to receive performance feedback parameters based on the packaged absorbent articles. The systems may correlate inspection parameters, process parameters, and performance feedback parameters with individual absorbent articles produced on the converting line. In turn, the controller may be configured to perform various functions based on the performance feedback parameters. For example, the controller may adjust target inspection parameters and/or the target process parameters based on the performance feedback parameters.

The systems and methods herein utilize technologies to create inspection and process monitoring systems with improved abilities to precisely correlate stored data with individual products produced from a converting line. In turn, performance feedback data obtained from individual products can be precisely correlated with the stored inspection and process data. The ability to precisely correlate inspection, process, and performance feedback data with individual products results in improved utilization of performance feedback data to effect desired adjustments in the converting process and to monitor the results of such adjustments. In some embodiments, the systems and methods may utilize feedback from technologies, such as vision systems, sensors, remote input and output stations, and controllers with synchronized embedded clocks to accurately correlate inspection results and measurements from an absorbent article converting process. These systems and methods may accurately apply the use of precision clock synchronization for both instrumentation and control system devices on a non-deterministic communications network, such as for example, an Ethernet IP network. In turn, the clock synchronized control and instrumentation network may be used to precisely correlate stored data with individual absorbent articles produced by a converting line. Thus, the controller may be programmed to track inspection data obtained from substrates and components as well as process data obtained from assembly equipment along the converting line without having to account for undeterminable delays.

It is to be appreciated that although the methods and apparatuses herein may be configured to manufacture various types of products, the methods and apparatuses herein are discussed below in the context of manufacturing absorbent articles. In particular, the methods and apparatuses are discussed in the context of manufacturing diapers. For the purposes of a specific illustration, FIG. 1 shows one example of a disposable absorbent article 100, such as described in U.S. Patent Publication Nos. US 2008/0132865 A1 and US 2011/0247199 A1, in the form of a diaper 102 that may be constructed from substrates and components monitored according to the systems and methods disclosed herein. In particular, FIG. 1 is a plan view of one embodiment of a diaper 102 including a chassis 104 shown in a flat, unfolded condition, with the portion of the diaper 102 that faces away from the wearer oriented towards the viewer. A portion of the chassis structure is cut-away in FIG. 1 to more clearly show the construction of and various features that may be included in embodiments of the diaper.

As shown in FIG. 1, the diaper 102 includes a chassis 104 having a first ear 106, a second ear 108, a third ear 110, and a fourth ear 112. The first ear 106 and second ear 108 may also be referred to herein as front ears 107. And the third ear 110 and the fourth ear 112 may be referred to as back ears 111. The back ears 111 may be connected with the chassis 104 with pressure bonds 150 such as shown for example in FIG. 1. To provide a frame of reference for the present discussion, the chassis 104 is shown with a longitudinal axis 114 and a lateral axis 116. The chassis 104 is shown as having a first waist region 118, a second waist region 120, and a crotch region 122 disposed intermediate the first and second waist regions. In some configurations, the first waist region 118 may correspond with a front waist region, and the second waist region 120 may correspond with a rear waist region. The periphery of the diaper is defined by a pair of longitudinally extending side edges 124, 126; a first outer edge 128 extending laterally adjacent the first waist region 118; and a second outer edge 130 extending laterally adjacent the second waist region 120. As shown in FIG. 1, the chassis 104 includes an inner, body-facing surface 132, and an outer, garment-facing surface 134. A portion of the chassis structure is cut-away in FIG. 1 to more clearly show the construction of and various features that may be included in the diaper. As shown in FIG. 1, the chassis 104 of the diaper 102 may include an outer covering layer 136 including a topsheet 138 and a backsheet 140. An absorbent core 142 may be disposed between a portion of the topsheet 138 and the backsheet 140. As discussed in more detail below, any one or more of the regions may be stretchable and may include an elastomeric material or laminate as described herein. As such, the diaper 102 may be configured to adapt to a specific wearer's anatomy upon application and to maintain coordination with the wearer's anatomy during wear.

The absorbent article may also include an elastic waist feature 143 shown in FIG. 1 in the form of a waist band 144 and may provide improved fit and waste containment. The elastic waist feature 143 may be configured to elastically expand and contract to dynamically fit the wearer's waist. The elastic waist feature 143 can be incorporated into the diaper and may extend at least longitudinally outwardly from the absorbent core 142 and generally form at least a portion of the first and/or second outer edges 128, 130 of the diaper 102. In addition, the elastic waist feature may extend laterally to include the ears. While the elastic waist feature 143 or any constituent elements thereof may comprise one or more separate elements affixed to the diaper, the elastic waist feature may be constructed as an extension of other elements of the diaper, such as the backsheet 140, the topsheet 138, or both the backsheet and the topsheet. In addition, the elastic waist feature 143 may be disposed on the outer, garment-facing surface 134 of the chassis 104; the inner, body-facing surface 132; or between the inner and outer facing surfaces. The elastic waist feature 143 may be constructed in a number of different configurations including those described in U.S. Patent Publication Nos. US 2007/0142806 A1; US 2007/0142798 A1; and US 2007/0287983 A1, all of which are hereby incorporated by reference herein.

As shown in FIG. 1, the diaper 102 may include leg cuffs 146 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 146 may be disposed in various ways on the diaper 102.

The diaper 102 may be provided in the form of a pant-type diaper or may alternatively be provided with a re-closable fastening system, which may include fastener elements in various locations to help secure the diaper in position on the wearer. For example, fastener elements 148 may be located on the third and fourth ears 110, 112 and may be adapted to releasably connect with one or more corresponding fastening elements located in the first or second waist regions. It is to be appreciated that various types of fastening elements may be used with the diaper.

Figure 2:
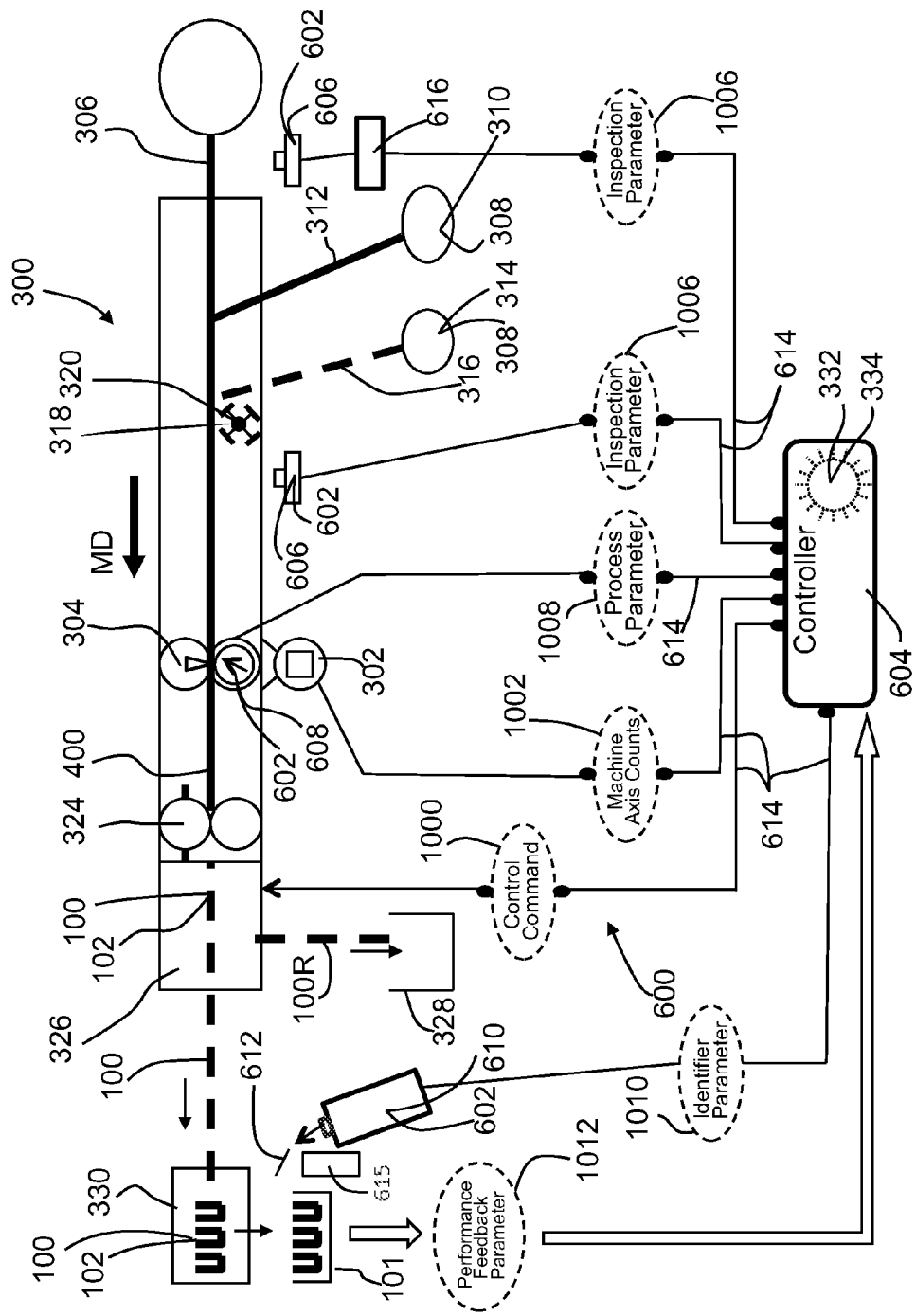
FIG. 2 is a schematic representation of an absorbent article converting line and control system.

FIG. 2 shows a schematic representation of an absorbent article converting process including a converting line or machine 300 configured to manufacture absorbent articles 100. It is to be appreciated that the systems and methods disclosed herein are applicable to work with various types of converting processes and/or machines. As shown in FIG. 2, the converting line 300 may include one or more motors 302 that drive transport systems, such as a nip roll 304, to move diaper substrates and component materials through the manufacturing process. For example, FIG. 2 shows a base substrate 306 and two auxiliary substrates and/or components 308 of material used to construct portions of the diapers. The substrates may be provided as rolls and fed into the converting line 300. It is to be appreciated that material of the auxiliary substrates may be supplied in various ways. For example, FIG. 2 shows a first auxiliary substrate 310 in the form of a continuous substrate 312, and a second auxiliary substrate 314 in the form of individual components 316. It is to be appreciated that the auxiliary substrates 310 may be transferred to the base substrate through various types of transfer mechanisms. For example, the individual components 316 may be in the form of ears 110, 112 such as shown in FIG. 1. As such, the individual ears 110, 112 may be transferred to the base substrate via a transfer mechanism 318 in the form of a servo patch placer mechanism 320, such as disclosed in U.S. Pat. Nos. 6,450,321; 6,705,453; 6,811,019; and 6,814,217. In addition, the nip roll 304 may be configured create the bonds 150 between the ears 110, 112 and the chassis 104. For example, the nip roll 304 may be configured as a mechanical bonding unit, such as disclosed in U.S. Pat. No. 4,854,984. In another example, the nip roll may be configured as a thermal bonding unit such as disclosed in U.S. Pat. No. 6,248,195. It is also to be appreciated that the various substrates can be used to construct various components of the absorbent articles, such as backsheets, topsheets, ears, leg cuffs, elastic waist features, and absorbent cores. Exemplary descriptions of absorbent article components are provided above with reference to FIG. 1.

Referring back to FIG. 2, as the base substrate 306 advances through the converting line 300, the base substrate 306 is combined with the auxiliary substrates 308 and/or discrete components 316 to create a continuous length of absorbent articles 400. At a downstream portion of the converting process 300, the continuous length of absorbent articles 400 is subjected to a final knife 324 and cut to create separate and discrete absorbent articles 100 in the form of diapers 102. Defective articles 100R may be subject to a rejection system 326 and removed from the process. For example, FIG. 2 shows defective articles 100R being channeled to a reject bin 328. It is to be appreciated that the term "reject bin" is used herein generically to designate the location where rejected diapers may be conveyed. As such, the reject bin 328 may include various systems. For example, the reject bin may 328 may include additional systems such as conveyors and/or pneumatic systems to provide additional transport or conveyance of rejected diapers to other locations. Articles 100 that are not deemed to be defective may be subject to further processing steps, such as folding and packaging. For example, FIG. 2 shows diapers 102 advancing from the final knife 324 to a packaging system 330 and placed into packages 101.

As shown in FIG. 2, an inspection system 600 may be configured to interact with, monitor, and/or control the converting line 300. As shown in FIG. 2 and as described in more detail below, various sensors 602 and other devices may be arranged adjacent the converting line 300 may communicate with a controller 604. Based on such communications, the controller 604 may monitor and affect various operations on the converting line 300. For example, the controller may send various types of control commands 1000 to the converter line, such as speed change commands based on communications with the sensors 602. In some embodiments, the control commands 1000 may be in the form of reject commands communicated to the reject system 326. In the systems and methods described herein, the controller 604 may include one or more computer systems. The computer system may, for example, include one or more types of programmable logic controller (PLC) and/or personal computer (PC) running software and adapted to communicate on an Ethernet IP network. Some embodiments may utilize industrial programmable controllers such as the Siemens S7 series, Rockwell ControlLogix, SLC or PLC 5 series, or Mitsubishi Q series. The aforementioned embodiments may use a personal computer or server running a control algorithm such as Rockwell SoftLogix or National Instruments Labview or may be any other device capable of receiving inputs from sensors, performing calculations based on such inputs and generating control actions through servomotor controls, electrical actuators or electro-pneumatic, electrohydraulic, and other actuators. Process and product data may be stored directly in the controller or may be located in a separate data historian. In some embodiments, the historian is a simple data table in the controller, in other embodiments, the historian may be a relational or simple database. Common historian applications include Rockwell Automation Factory Talk Historian, General Electric Proficy Historian, OSI PI, or any custom historian that may be configured from Oracle, SQL or any of a number of database applications.

As the substrates and components travel in the machine direction MD through the converting line, the controller 604 tracks the advancement of the substrates and components. In some embodiments such as shown in FIG. 2, the controller 604 may track the advancement with counts generated by a machine axis 332 that correspond with machine direction positions on substrates and components while advancing though the converting line 300. In some configurations, the machine axis 332 may be configured as an actual motor 302 that provides count signals 1002 to the controller 604. The controller 604 may utilize rotational speed, time, and/or count data from the machine axis 332 that correspond with the machine direction speed and travel of the substrates and components through the converting line 300.

It is to be appreciated that instead of or in addition to utilizing feedback from a physical machine axis as discussed above, the rotational motion of the machine axis 332 may be simulated by software in the controller. For example, in FIG. 2, the controller 604 can utilize counts generated by a virtual machine axis 334 in the controller software. More particularly, the virtual machine axis 334 may be programmed to imitate a motor that generates counts as the motor rotates. As such, it is to be appreciated that the machine axis 332 referred to herein may be either a virtual axis existing in software or a physical axis corresponding with the rotational motion of a motor or other equipment.

Figure 3:
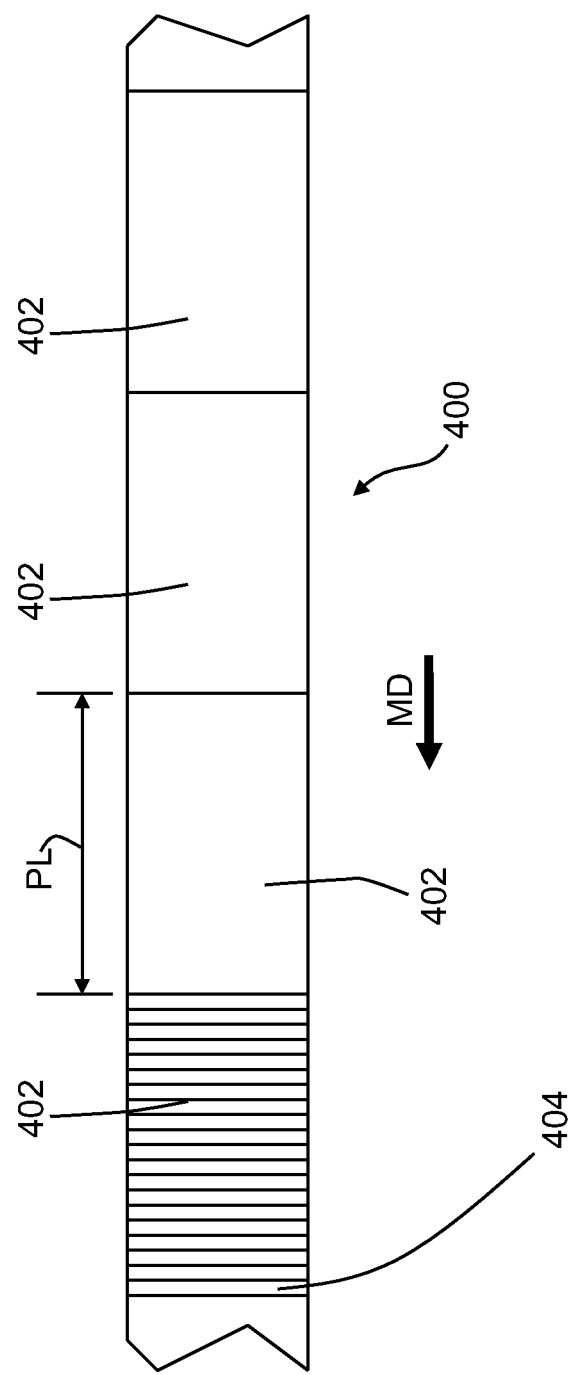
FIG. 3 is a top view of an advancing substrate showing virtual products and virtual segments.

As discussed above, the machine axis 332 may be configured to correlate the linear motion of the substrates and components in the machine direction MD through the converting line 300 with counts corresponding with rotation of the machine axis 332. In some embodiments, one complete rotation of the machine axis 332 and associated count data correspond with one pitch length of an absorbent article 100. In some embodiments, the pitch lengths of the absorbent articles are the machine direction longitudinal lengths of the individual absorbent articles being produced. FIG. 1 shows an example of a longitudinal pitch length PL of a diaper. As such, the controller 604 may use counts generated from the machine axis 332 to virtually divide the substrates and components into virtual products 402. As shown in FIG. 3, the virtual products 402 may have machine direction lengths PL that correspond with the pitch lengths PL of products being produced. For example, FIG. 3 shows a top side view of the base substrate 306 divided into virtual products 402 along the machine direction MD by the controller 604. Count signals corresponding with rotation of the machine axis that correspond with less than a complete rotation can also be used by the controller divide each virtual product 402 into virtual segments 404, such as shown in FIG. 3. As discussed in more detail below, the substrate speed and estimated clock inaccuracies can be used to determine the length of the each virtual segment in the machine direction MD, and in turn, the number of virtual segments in each virtual product. For example, FIG. 3 shows one virtual product 402 divided into twenty virtual segments 404. As discussed in more detail below, the controller 604 can also utilize signals from the sensor 602 that correspond with the detection of various parameters in virtual products and segments to correlate the locations of parameters within manufactured products 100.

As previously mentioned, the systems and methods herein utilize various types of sensors 602 to monitor the substrates and components traveling through the converting line. As shown in FIG. 2, sensors 602 may be configured as inspection sensors 606 to monitor various aspects in the substrates 106, 108, 110 and/or components 116. In some configurations, the inspection sensors 606 may detect defects within substrates and/or components themselves, such as for example, damage, holes, tears, dirt, and the like, and may also detect defective assemblies and/or combinations of the substrates and components, such as for example, missing and/or misplaced ears, landing zones, fasteners, and the like. As such, inspection sensors 606 may be configured to detect the presence or absence of substrates and/or components, and may be configured to detect the relative placement of substrates and/or components. As discussed in more detail below, based on the detections of the inspection sensors 606, feedback signals from the inspection sensors 606 in the form of inspection parameters 1006 are communicated to the controller 604.

It is to be appreciated that various different types of inspection sensors 606 may be used to monitor substrates and various components while advancing through the converting line 300. For example, inspection sensors 606 may be configured as photo-optic sensors that receive either reflected or transmitted light and serve to determine the presence or absence of a specific material; metal-proximity sensors that use electromagnetic to determine the presence or absence of a ferromagnetic material; or capacitive or other proximity sensors using any of a number of varied technologies to determine the presence or absence materials. Inspection sensors 604 may also be configured as vision systems and other sub-processing devices to perform detection and, in some cases, logic to more accurately determine the status of an inspected product. Particular examples of such inspections sensors 606 may include Cognex Insight, DVT Legend or Keyence smart cameras, component vision systems such as National Instruments PXI or PC based vision system such as Cognex VisionPro or any other vision system software which can run on a PC platform.

It should also be appreciated that inspection parameters 1006 may be provided from inspection sensors 606 in various forms. In one embodiment, inspection parameters 1006 may be in the form of "results," such as for example, provided from a sensor state change resulting in a binary input corresponding with the detected presence or absence of a defect, such as for example, the presence or absence of components and/or substrates. For example, inspection parameters 1006 may indicate the presence or absence of an ear, landing zone, and/or printed graphics on a product. In another example, an inspection parameter 1006 may indicate the presence or absence of a tear, hole, splice tape, and/or contaminants in a substrate and/or component. In another embodiment, inspection parameters 1006 may be provided in the form of measurements and/or numerical indications of detected positions of components and/or substrates; numerical indications of the positions of components and/or substrates relative to other components and/or substrate; and/or numerical indications of the positions of components and/or substrates relative to another physical or virtual reference. For example, inspection parameters 1006 may indicate the relative position of one feature, such as a back ear fastener, with respect to a back ear substrate or the measured width of a main chassis compared to the desired width. In other embodiments, inspection parameters 1006 may be in the form of images transferred via a standard protocol such as ftp (File Transfer Protocol), DDE (Dynamic Data Exchange), or OPC (Object Linking and Embedding for Process Control), which are stored in a database or stored in a specified directory on an image server for the purpose of either operator visualization, offline image processing or claim support.

As previously mentioned, the systems and methods herein utilize various types of sensors 602 or data from the controller 604 to monitor the various assembly equipment used in the converting line 300. As shown in FIG. 2, equipment sensors 602 may be configured as process sensors 608 to monitor various aspects of process equipment or operations. In some configurations, the process or equipment sensors may be linear position transmitters, rotary position transmitters, rotational encoders for speed and position feedback, temperature sensors such as RTD elements, pressure and/or vacuum transmitters or vibration sensors. Controller data may be configured as data from drive position or velocity control loop, automatic or operator induced control actions, motor current or power or any other parameter that can be harvested from a controller 604. As discussed in more detail below, based on the detections of the process sensors 608, feedback signals from the process sensors 608 in the form of process parameters 1008 are communicated to the controller 604.

In addition to the inspection sensors 606 and process sensors 608, the systems and methods herein may utilize various types of sensors 602 to identify the absorbent articles 100 that are produced. For example, as shown in FIG. 2, some sensors 602 may be configured as product identifier sensors 610 that are adapted to identify products 100 manufactured by the converting line 300. Based on the detections of the product identifier sensors 610, feedback signals from the product identifier sensors 610 in the form of identifier parameters 1008 are communicated to the controller 604 and further to a historian. In some configurations, a unique identifier may be applied to each individual diaper 102 that are detected by the product identifier sensors 610. It is to be appreciated that the unique identifier may be configured in various ways, such as for example, a serial number, a bar code, and/or a QR code. Further, the unique identifier could be a combination of identifiers that, in combination, can serve to uniquely identify the product. It is also to be appreciated that a unique identifier may also be applied to a bundle of individual diapers 102, or to a package 101 containing multiple individual diapers 102. In some instances, the system 600 may be configured to add individual preprinted inserts 612 from a dispenser 615 into stacks of diapers 102 before being packaged. The product identifier sensor 610 may be configured as a scanner that senses a unique identifier in the form of a 1D or 2D code on the inserts 612 as the inserts are packaged with the diapers 102. In some instances, the system 600 may be configured to add individual preprinted stickers 612 from a dispenser 615 onto the bag of diapers 102 before being packaged. The product identifier sensor 610 may be configured as a scanner that senses a unique identifier in the form of a 1D or 2D code on the sticker 612 as the stickers are applied to the package 102.

It is also noted that the unique identification process may utilize, but does not require a sensor 602 to detect the applied unique identifier. In some embodiments, the unique identifier could be applied in such a way that the identifier parameter 1010 can be stored in the historian. For example, if a printer is used to print a unique identifier, such as a serial number or an accurate time-stamp, the commanded print string can be stored as identifier parameter 1010 without directly sensing the identifier data on the product or package. Product performance feedback is then correlated to the unique product identifier as determined by direct human observation.

As shown in FIG. 2, the sensors 602, such as the inspection sensors 606, process sensors 608, and product identifier sensors 610, may be connected with the controller 604 and historian through a communication network 614, which allows the inspection sensors 606, process sensors 608, and product identifier sensors 610 to communicate inspection parameters 1006, process parameters 1008, and identifier parameters 1010, respectively, to the controller 604. As discussed in more detail below, devices that communicate on the network each include precision clocks that are synchronized to a master clock within some specified accuracy. As shown in FIG. 2, the sensors 602 and the controller 604 may be connected directly with the communication network 614. As such, each sensor or other field device connected directly with the communication network may include a clock. Sensors 602 that include a clock and that may be connected directly with the communication network 614 may include, for example, vision systems such as National Instruments CVS or any PC-based vision system such as Cognex VisionPro. Such sensors may also include other controllers that may be configured as peers to the controller or may be configured as subordinate to the controller.

In some embodiments, the sensors 602, such as the inspection sensors 606, process sensors 608, and product identifier sensors 610, may be indirectly connected with the communication network 614. For example, the inspections sensors 602 may be connected with the communication network 614 through a remote input and output (I/O) station 616. When utilizing remote I/O stations 616, the sensors 602 may be hardwired to the remote I/O stations, and in turn, the remote I/O stations are connected with the communication network 616. As such, the each remote I/O station 616 may include a precision clock. Example remote I/O stations 616 or other IEEE-1588 based instruments that can be utilized with systems and methods herein include, for example a National Instruments PCI-1588 Interface (IEEE 1588 Precision Time Protocol Synchronization Interface) that synchronizes PXI systems, I/O modules and instrumentation over Ethernet/IP or a Beckhoff Automation EtherCat and XFC technology (eXtreme Fast Control Technology).

As previously mentioned, each device, such as the inspection sensors 606, process sensors 608, product identifier sensors 610, remote I/O stations 616, and the controller 604, connected with the communication network 614 includes a clock, and each clock is synchronized to a master clock. In one configuration, the controller 604 includes the master clock, and all other clocks of devices connected with the communication network are referenced to the controller master clock. In such a configuration, the remote I/O stations, inspection sensors, process sensors, and product identifier sensors each include a clock that is synchronized to the controller master clock. For example, inspection parameters 1006 provided by the inspection sensors 606 and process parameters 1008 provided by the process sensors 608 communicated to the communication network 614 are time-stamped with the time from the clocks on the corresponding sensors and remote I/O stations. Similarly, identifier parameters 1010 provided by the product identifier sensors 610 communicated to the communication network 614 are time-stamped with the time from the clocks on the corresponding sensors and remote I/O stations. In turn, the inspection parameters, process parameters, identifier parameters, and corresponding time-stamp data are sent to the controller 604 over the communication network 614. Thus, the controller 604 can be programmed to correlate the inspection parameters, process parameters, and identifier parameters based on the actual time the parameters were provided by the respective sensors. Therefore, ambiguity as to when detections were actually made by respective sensors is relatively small. Additionally, traditional methods of storing inspection parameters, process parameters, and identifier parameter normally rely on OPC (Object Linking and Embedding for Process Control) to pass data which is subsequently time-stamped at the destination, for example, a computer housing the historian. With these methods, the transport delays between the data source and the clock drift of the computer housing the historian combine to create further ambiguity in the detection time-stamp of the data.

The controller may 'normalize' the time-stamps by adjusting the reported time-stamps which were recorded at the time of detection to a reference location in the process. In this manner, all data may be correlated to the production time (normalized time) of the particular product on which the measurement was detected. For example, if an inspection is performed using an inspection system 600, which may include a vision system, at some location in the process, and equipment parameters are recorded by a process sensor 602 at a second location in the process and the unique product identifier parameter 1010 are recorded at a third location in the line, the controller may adjust each time-stamp in such a way that all three parameters will have the same time-stamp and therefore be correlated to the same individual product. Further, if some product is removed from the production in order to perform offline manual inspections, the system can be configured to record the sample time of the product being removed, to adjust that time-stamp to the normalized time of that individual product and to present that time-stamp to the quality assurance laboratory, who may use that time-stamp when that data is stored in the historian. By recording the time-stamp at the moment of detection, normalizing it to a reference point in the process and passing the normalized time-stamp to the historian as the associated data time-stamp, the majority of the ambiguities in the system are eliminated.

As previously mentioned, all clocks that are used to determine and report time-stamps may be synchronized together. Clock synchronization allows the reported time from one device on the communication network 614 to be utilized by another device on the communication network. When the clocks are synchronized, ambiguity as to when parameters were actually provided by the respective sensors 602 is affected only by the accuracy of the clocks with respect to each other. The clocks of the devices on the communication network may be synchronized in various ways depending on the type of communication network 614 used.

In one embodiment, the communication network 614 is configured as a non-deterministic communication network, such as for example, Ethernet or Ethernet IP (industrial protocol) communication network. When using an Ethernet IP communication network, the clocks of each device may be synchronized using the IEEE1588 precision time protocol, described in IEEE1588 Standard, "Precision Clock Synchronization Protocol for Networked Measurement and Control Systems" and also described in Rockwell Automation publication number 1756-WPO05A-EN-E, published January 2009, and entitled "An Application of IEEE 1588 to Industrial Automation." As mentioned above, time-stamps associated with parameters from any sensor may be referenced to the master clock, which allows the relative time as to when the inspection parameters were provided to be accurately calculated. In one configuration, the controller includes the master clock, the controller master clock, and all other clocks of devices connected with the communication network, the sensor clocks, are referenced to the controller master clock. As a result, the time as to when inspection parameters, process parameters, and identifier parameters were provided from respective sensors can be can be reported to the controller within the accuracy of an IEEE1588 compliant clock. In some embodiments, reported time-stamps may be accurate to within 0.1 milliseconds of the controller master clock. In another configuration, another device, such as an Ethernet switch or router is the local master clock. In this case, both the controller clock and the sensor clock follow the local master clock. The identity of the local master is unimportant since all clocks in the system are synchronized to the local master within the IEEE1588 PTP standard.

With reference to the above description and figures, the methods and systems herein utilize a controller 604 and one or more sensors 602, such as inspection sensors 606, process sensors 608, and product identifier sensors 610, connected with a communication network 614. Each sensor 602, and remote I/O device 616, if used, have clocks that are synchronized with the master controller clock in the controller. The controller 604 tracks the movement of the substrates and components traveling in the machine direction of the converting line 100. More particularly, controller 604 utilizes feedback from the machine axis 332 to virtually divide the substrates and components into virtual products 402 along the machine direction, track the movement of virtual products 402 in the machine direction, and correlate the virtual products 402 to actual individual products 100, 102 produced after being cut by the final knife 324. In addition, the controller 604 utilizes feedback from the machine axis 332 to virtually divide the virtual products 402 into virtual segments 404 along the machine direction.

During manufacture, the inspection sensors 606 provide inspection parameters 1006 to the controller 604 via the communication network 614. As discussed above, the inspection parameters 1006 can be configured to indicate various types of information, such as measurement data and/or images, about the substrates and/or components. The inspection sensors 606 provide inspection parameters 1006 to the communication network along with associated time-stamp from the sensor clocks. Similarly, the process sensors 608 provide process parameters 1008 to the controller 604 via the communication network 614. As discussed above, the process parameters 1008 can be configured to indicate various types of information, such as temperatures and/or pressures, from the assembly equipment on the converting line 300. In turn, the process sensors 608 provide inspection parameters 1008 to the communication network along with associated time-stamp from the sensor clocks. In addition, the product identifier sensors 610 provide identifier parameters 1010 to the controller 604 via the communication network 614. As discussed above, the identifier parameters 1010 can be configured to identify individually produced articles 100, 102 once placed in packages 101 and that the associated time-stamps may be normalized to facilitate that correlation. In turn, the product identifier sensors 610 provide identifier parameters 1010 to the communication network along with associated normalized time-stamp from the sensor clocks. The controller 604 receives the inspection parameters 1006, process parameters 1008, identifier parameters 1010, and associated time-stamps from the communication network 614 and correlates the inspection parameters 1006 and process parameters 1008 with the corresponding virtual products 150 and/or virtual segments 152 moving along the converting line 300, and in turn, with individual products 100, 102 in a package 101.

It should be noted that while time-stamps, and specifically normalized time-stamps are an efficient method to provide correlation between process data, inspection parameters and product performance feedback, other techniques to make the correlation may be used. For example, the product's unique identifier may be a mathematical sequence. The controller 604 and inspection devices 616 may independently generate the same sequence. When data is stored from varied sources, each piece of data is identified by the product unique identifier rather than a time.

As discussed above, the controller 604 may also be adapted to receive performance feedback parameters 1012. Performance feedback parameters may be generated in various ways and may include various information and/or data relating to the articles 100, 102 produced by the converting line 300. For example, performance parameters 1012 may generated as a result of laboratory testing and/or consumer feedback. In some configurations, performance parameters 1012 may be generated in a laboratory environment where absorbent articles may be disassembled and subjected to various tests. In some configurations, performance parameters 1012 may be collected as a result of soliciting and recording consumer feedback relating to in use performance of the packaged absorbent articles. Examples of performance parameters 1012 may include data relating to the separation of back ears from diapers while under tension; leakage; component alignment; and absorbent article fit. It is to be appreciated that consumer feedback may include any kind of information provided by the consumer as end-user which is or may be relevant to product quality data. Consumer feedback includes, for example, responses to questionnaires or interviews, complaints made by dissatisfied customers, any of which may be may be recorded in written form, or as audio or video recording; and/or images of product in use or after use. Performance parameters may be transmitted directly from feedback providers to the controller in various ways, such as via written communication; electronic communication; internet interface; and/or combinations thereof. As such, performance parameters can be communicated with various types of devices, such as telephones; computers; mobile devices such as mobile telephones; smart phones; tablets; and the like. Performance parameters may also be transmitted in various ways feedback providers to intermediaries, which can then communicate and/or enter the performance parameters into the controller.

Figure 4:
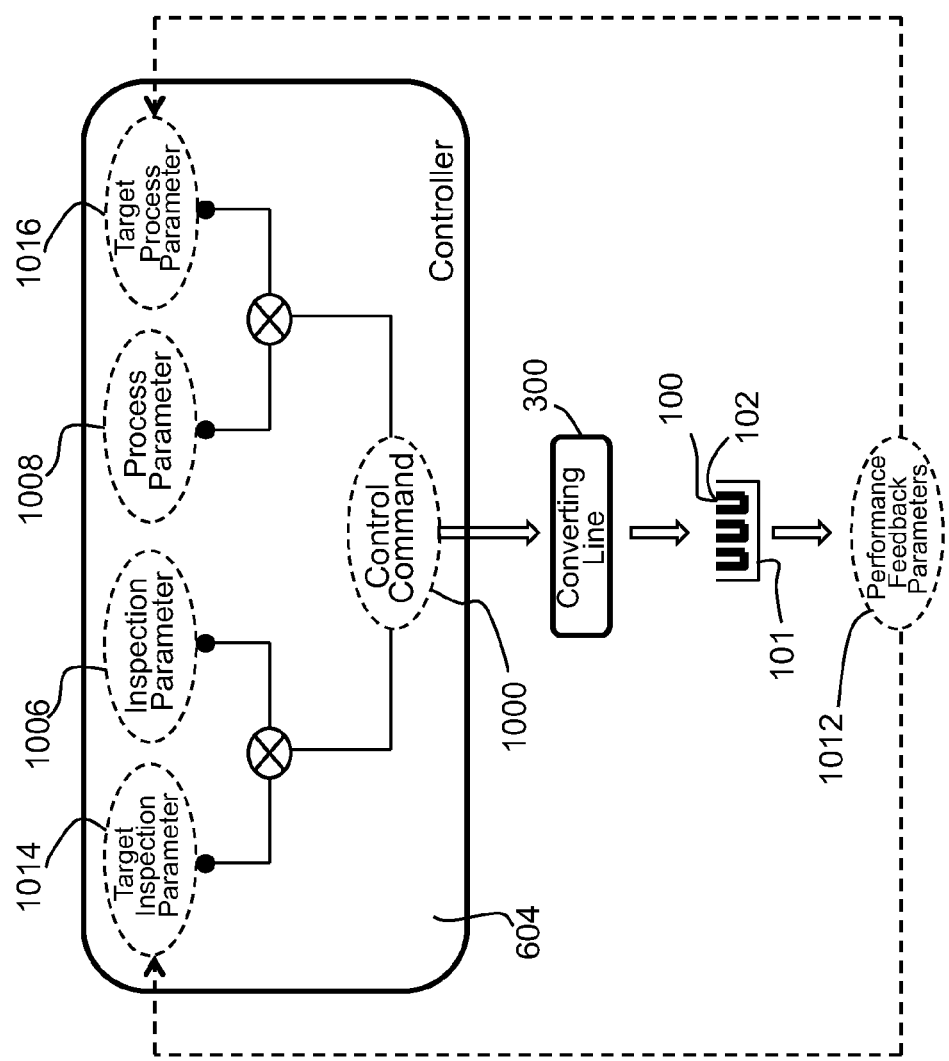
FIG. 4 is a block diagram showing how target inspection parameters and target process parameters may be adjusted based on performance feedback parameters.

As previously mentioned, the controller 604 may be adapted to send various types of control commands 1000 to the converting line 300, such as for example, speed change commands, reject commands, and shutdown commands. Such control commands 1000 may be based on parameters communicated from various sensors 602 as described above. For example, control commands 1000 may be based on inspection parameters 1006 and/or process parameters 1008 provided by inspection sensors 606 and process sensors 608. In the example block diagram shown in FIG. 4, the controller 604 may include target inspection parameters 1014 and/or target process parameters 1016. During the manufacturing process, the controller 604 compares inspection parameters 1008 to corresponding target inspection parameters 1014 to generate control commands 1000 to control various operations on the converting line 300. Similarly, the controller 604 compares process parameters 1008 to corresponding target process parameters 1016 to generate control commands 1000 to control various operations on the converting line 300. As described above, performance feedback parameters 1012 that may include various types of information and/or data relating to the articles 100, 102 produced by the converting line 300 are communicated to the controller 604. The performance feedback parameters 1012 can then be used as a basis to adjust the target inspection parameters 1014 and/or target process parameters 1016. Because the inspection parameters 1006, process parameters 1008, and performance feedback parameters 1012 are correlated with each other and to specific articles 100, 102, the resulting affects in how articles 100, 102 are manufactured can be observed and relatively more precisely correlated with adjusted parameters. As discussed in the example below, correlated performance feedback parameters 1012, correlated inspection parameters 1006, and correlated process parameters 1008 may be used to adjust target inspection parameters 1014 and/or target process parameters 1016 to harmonize quality specification limits with feedback from various sources, such as for example, consumers, line operators, process design personnel, and/or product design personnel.

To provide additional context to the above discussion, the following provides a specific description of an example implementation of the systems and processes herein. FIGS. 5A-6D show an example of an absorbent article converting line 300 as substrates and components travel along the machine direction MD through a nip roll 304, a final knife 324, and a packaging system 330. In particular, FIGS. 5A-5D show schematic side views of the converting line 300, substrates 306, 308 and components 316 assembled into a continuous length of absorbent articles 400. And FIGS. 6A-6D show a plan view of the continuous length of absorbent articles 400 and virtual absorbent articles 402 that correspond with FIGS. 5A-5D, respectively. For the purposes of the discussion relating to FIGS. 5A-6D, the converting line 300 is described in the context of a diaper converting line. In particular, a base substrate 306 is shown to enter and advance in the machine direction MD through the converting line 300. Material from an auxiliary substrate 308 is cut into individual components 316, transferred to the base substrate 306 to form features on the base substrate 306, such as for example, back ears 111 on a diaper. The back ears are also shown as being bonded to the base substrate 306 at nip roll 304, which may be in form of a mechanical bonding unit as discussed above. As such, the nip roll 304 may be configured create the bonds 150 between the back ears 111 and the base substrate 306, such as shown in FIGS. 6B-6D.

FIGS. 5A-5D also show an inspection sensor 606, a process sensor 608, product identifier sensor 610, controller 604, machine axis 332, packaging system 330, and packages 101 containing multiple individual diapers 102. In accordance with the above description, the machine axis 332 is shown schematically in the form of a virtual axis 334 and provides base substrate position and speed signals to the controller 604. In turn, the controller 604 divides the base substrate into virtual products 402 along the machine direction MD, such as described above with reference to FIG. 3. Also in accordance with the above discussion, the inspection sensor 606, process sensor 608, and product identifier sensor 610 are each connected with remote I/O stations 616. In turn, the remote I/O stations 610 and controller 142 are connected with a communication network 614, in the form of an Ethernet IP network. It is to be appreciated that various quantities of sensors 602 may be used and that some or all sensors may be connected directly with the communication network 614 without using remote I/O stations. Each remote I/O station 616 includes a clock 1018, referred to herein as a sensor clock 1020 providing a time, Ts, and the controller includes a clock 1018, referred to herein as the master control clock 1022 providing a time, Tc. The sensor clocks 1020 are synchronized with the master control clock 1012, such that Ts is set to equal Tc. For the purposes of the present discussion, the lengths of the virtual products 402 in the machine direction correspond with the pitch lengths PL of products 102 being produced. In the present example, it may be assumed that the machine axis 332 rotates such that one complete one rotation corresponds with a one pitch length advancement of the base substrate 306 in the machine direction. Upon each revolution of the machine axis 332, a shift register in the controller 604 is incremented by one virtual product 402. The aforementioned increments continue as the base substrate 306 advances through the converting line 300.

FIGS. 5A-5D show the advancement of the base substrate 106 in the machine direction through the mechanical bonding unit 304 and past the inspection sensor 606. As discussed above, the inspection sensor 606 can be configured to perform various detection operations. In one example, the inspection sensor 606 may be configured as a vision system that detects an inspection parameter that is indicative of the quality of bonds 150 between the back ears 111 and the base substrate 306 passing thereby. As such, the inspection sensor 606 provides an inspection parameter 1006 to the communication network via the remote I/O station, wherein the inspection parameter 1006 corresponds with sensed relative strengths of the individual bonds 150. In accordance with the above discussion, the inspection parameter 1006 includes a corresponding time-stamp from the sensor clock 1020. When the position of the inspection sensor 606 along the converting line 300 is known by the controller 604, the controller 604 can correlate the inspection parameters 1006 provided by the inspection sensor 606 with the corresponding virtual products 402 based on the normalized time-stamps of the inspection parameters 1006.

FIGS. 5A-5D also show a process sensor 608 operatively connected with the mechanical bonding unit 304. As discussed above, the process sensor 608 can be configured to perform various detection operations. In one example, the process sensor 608 may be configured as a pressure sensor that detects the applied pressure of the mechanical bonding unit 304. As such, the process sensor 608 provides a process parameter 1008 to the communication network via the remote I/O station, wherein the process parameter 1008 corresponds with the sensed pressure of the mechanical bonding unit 304 while creating the bonds 150 between the back ears 111 and the base substrate 306. In accordance with the above discussion, the process parameter 1008 includes a corresponding time-stamp from the sensor clock 1020. When the position of the pressure sensor 608 along the converting line 300 is known by the controller 604, the controller 604 can correlate the process parameters 1008 provided by the inspection sensor 608 with the corresponding virtual products 402 based on the normalized time-stamps of the process parameters 1008. In turn, the controller 604 can correlate the process parameters 1008 and inspection parameters 1006 with virtual products 402. Thus, the controller is able to correlate the sensed pressures from the mechanical bonding unit 304 on a virtual product advancing through the mechanical bonding unit with the sensed presence and/or absence of bonds 150 on the same virtual product.

With continued reference to FIGS. 5A-5D, the inspection system 600 also includes a product identifier sensor 610 adapted to identify diapers 102 manufactured by the converting line 300. As discussed above, a unique identifier may be applied to each individual diaper 102 that are detected by the product identifier sensors 610. The unique identifier may be configured in various ways, such as for example, a serial number, a bar code, and/or a QR code. As such, the product identifier sensor 610 provides an identifier parameter 1010 to the communication network via the remote I/O station, wherein the identifier parameter 1010 corresponds with the unique identifier on a diaper 102. In accordance with the above discussion, the identifier parameter 1010 includes a corresponding time-stamp from the sensor clock 1020. When the position of the product identifier sensor 610 along the converting line 300 is known by the controller 604, the controller 604 can correlate the identifier parameters 1010 provided by the product identifier sensor 610 with the corresponding virtual products 402 based on the normalized time-stamps of the identifier parameters 1010. In turn, performance feedback parameters 1012 and associated unique identifiers can be sent to and received by the controller 604 and historian, which can then correlate process feedback parameters 1012 with the process parameters 1008 and inspection parameters 1006 of virtual products 402. Thus, for example, the controller is able to correlate product performance information, such as for example, failures of the bonds 150 during diaper usage, with the sensed pressures on the mechanical bonding unit 304 on a virtual product 402 and the sensed quality, presence, and/or absence of bonds 150 on the same virtual product 402.

Figure 5A:
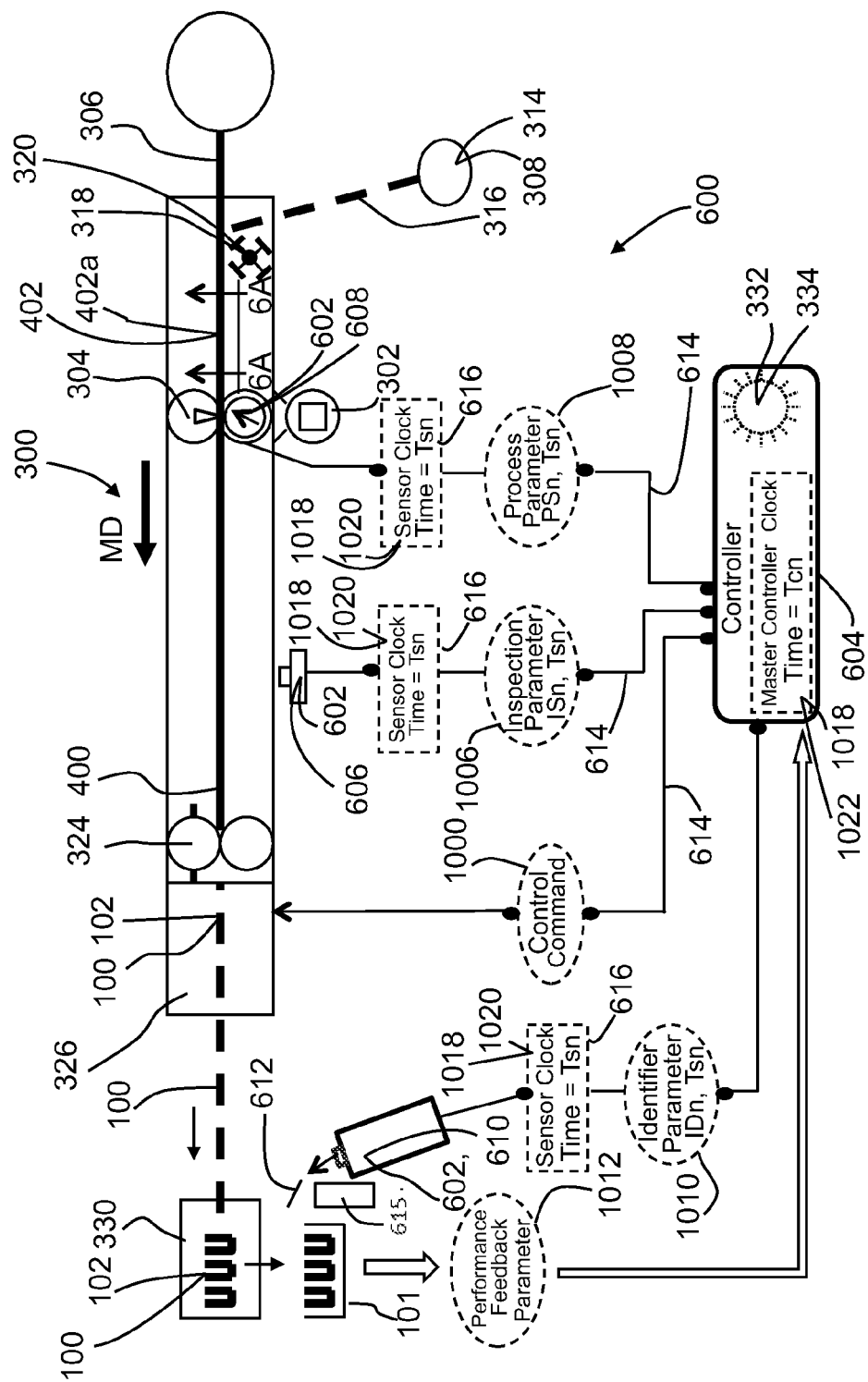
FIG. 5A is a schematic representation of an implementation of an absorbent article converting line and control system.
Figure 5B:
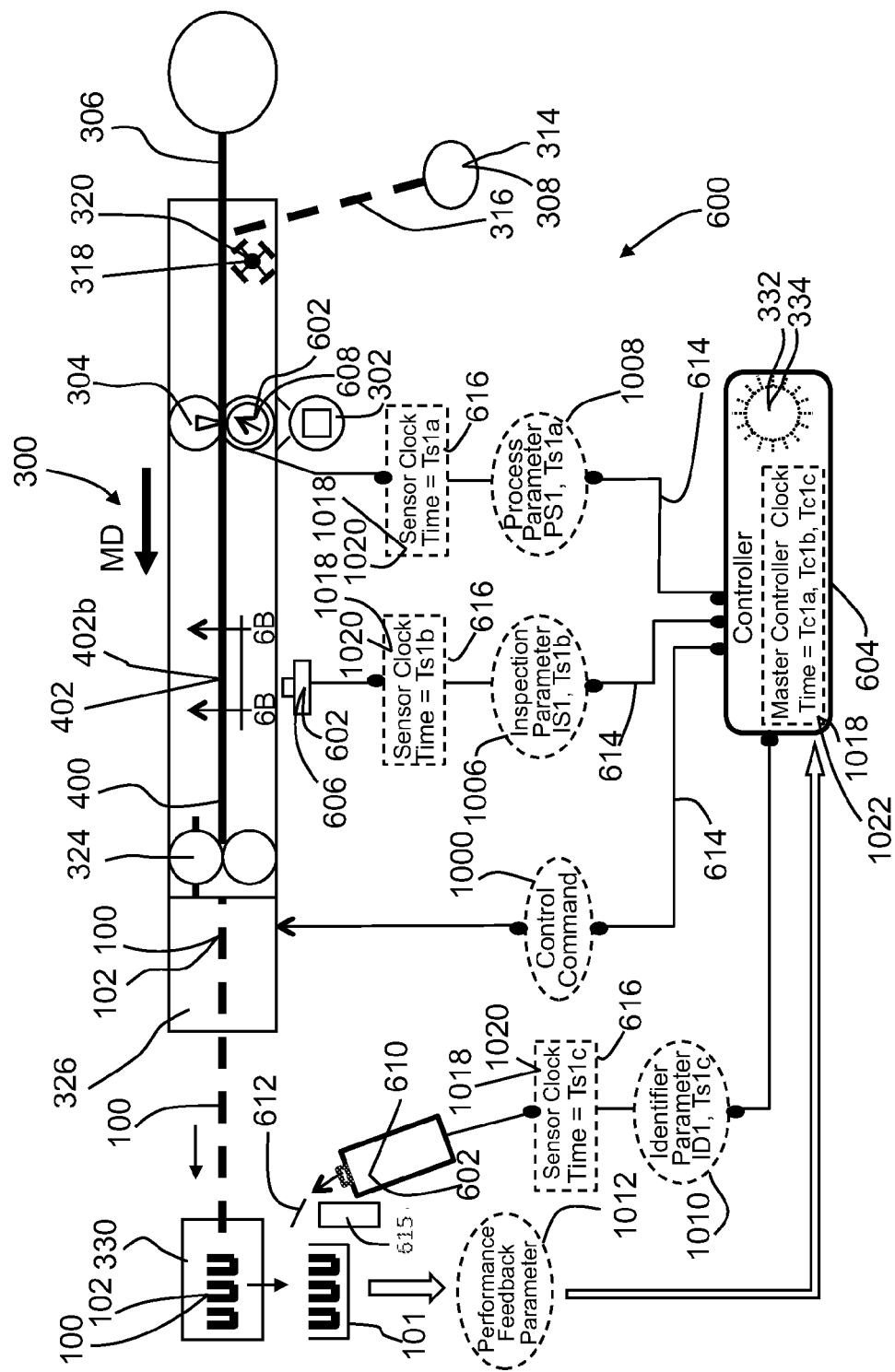
FIG. 5B is a schematic representation of an implementation of an absorbent article converting line and control system.

FIGS. 5A and 6A show the advancement of the base substrate in the machine direction, and in particular, advancement of a first virtual product 402a to the mechanical bonding unit 304. FIGS. 5B and 6B show the continued advancement of the base substrate in the machine direction, and in particular, advancement of a second virtual product 402b past the inspection sensor 606. As shown in FIG. 6B, two back ears 111 are connected with bonds 150 to the base substrate 306. The bonds 150 are schematically represented by discrete, black crescent-shaped areas. As shown in FIG. 6B six bonds 150 are shown to connect a first back ear 111a with the base substrate 306, and six bonds 150 are shown to connect a second back ear 111b with the base substrate. FIG. 5B shows a first process parameter PS1 having a corresponding time stamp, Ts1a, being communicated to the communication network 614. PS1 may be configured to provide an indication of the applied pressure of the mechanical bonding unit 304 while creating the bonds 150 on the second virtual product 402b. Simultaneously, the time reported by master controller clock 1022 is Tc1a. A first inspection parameter, IS1, having a corresponding time-stamp, Ts1b, is also being communicated to the communication network 614. IS1 may be configured to provide an indication of the quality and presence of bonds 150 on the second virtual product 402b. Simultaneously, the time reported by master controller clock 1022 is Tc1b. In addition, a first identifier parameter, ID1, having a corresponding time-stamp, Ts1c, is being communicated to the communication network 614. ID1 may be configured to provide an indication of the unique identifier on the second virtual product 402b. Simultaneously, the time reported by master controller clock 1022 is Tc1c. As discussed below, PS1, IS1, and ID1 may not be immediately received by the controller 604.

Figure 5C:
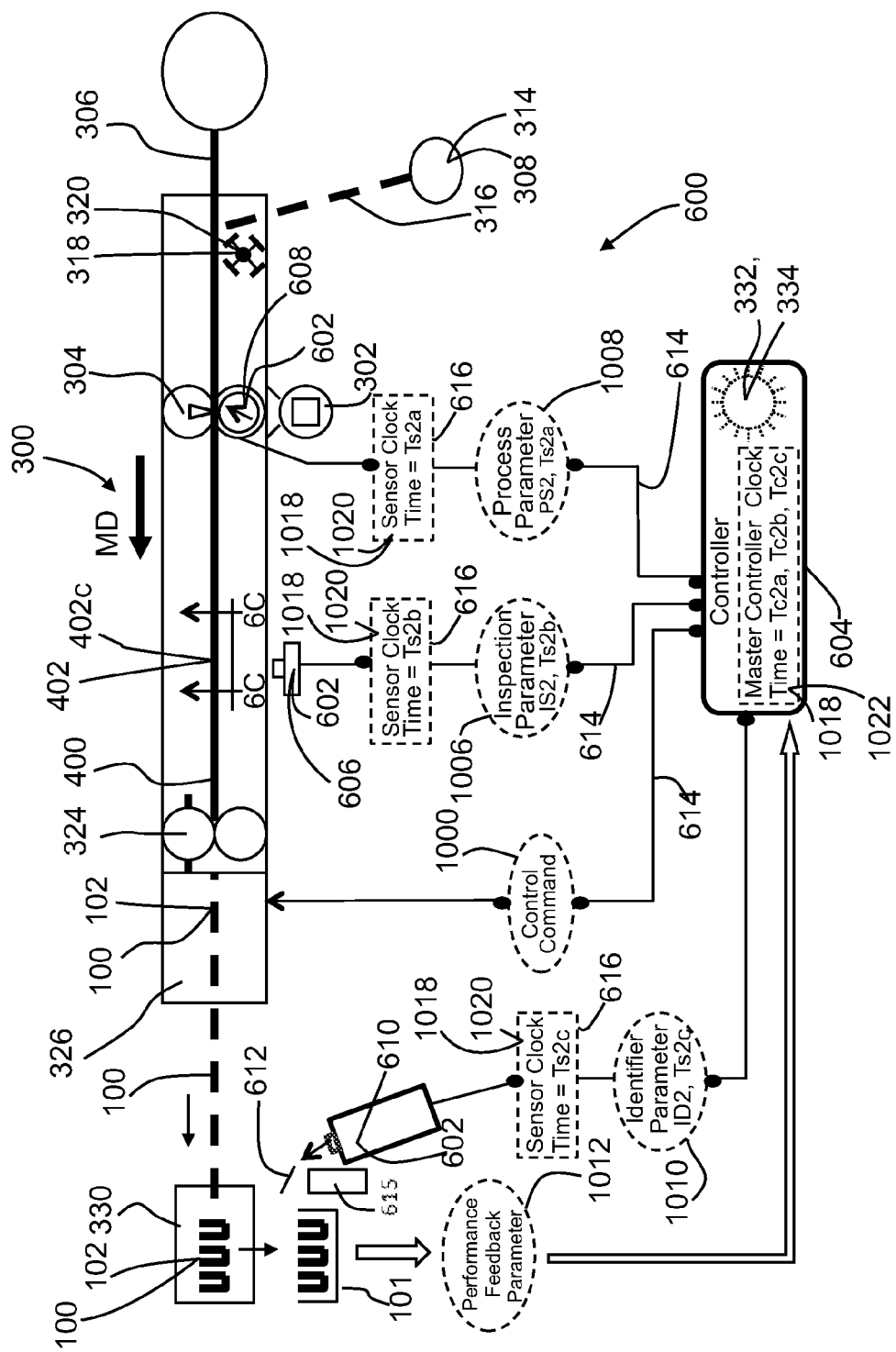
FIG. 5C is a schematic representation of an implementation of an absorbent article converting line and control system.

Next, FIGS. 5C and 6C show the continued advancement of the base substrate 306 in the machine direction MD, and in particular, advancement of a third virtual product 402c past the inspection sensor 606. FIG. 5C shows a second process parameter PS2 having a corresponding time stamp, Ts2a, being communicated to the communication network 614. PS2 may be configured to provide an indication of the applied pressure of the mechanical bonding unit 304 while creating the bonds 150 on the third virtual product 402c. Simultaneously, the time reported by master controller clock 1022 is Tc2a. A second inspection parameter, IS2, having a corresponding time-stamp, Ts2b, is also being communicated to the communication network 614. IS2 may be configured to provide an indication of the quality and presence of bonds 150 on the third virtual product 402c. In particular, IS2 may provide an indication of the degraded quality of bonds 150 on the first back ear 111a, represented by the three discrete, gray crescent-shaped areas in FIG. 6C. Simultaneously, the time reported by master controller clock 1022 is Tc2b. In addition, a second identifier parameter, ID2, having a corresponding time-stamp, Ts2c, is being communicated to the communication network 614. ID2 may be configured to provide an indication of the unique identifier on the third virtual product 402c. Simultaneously, the time reported by master controller clock 1022 is Tc2c. As discussed below, PS2, IS2, and ID2 may not be immediately received by the controller 604.

Figure 5D:
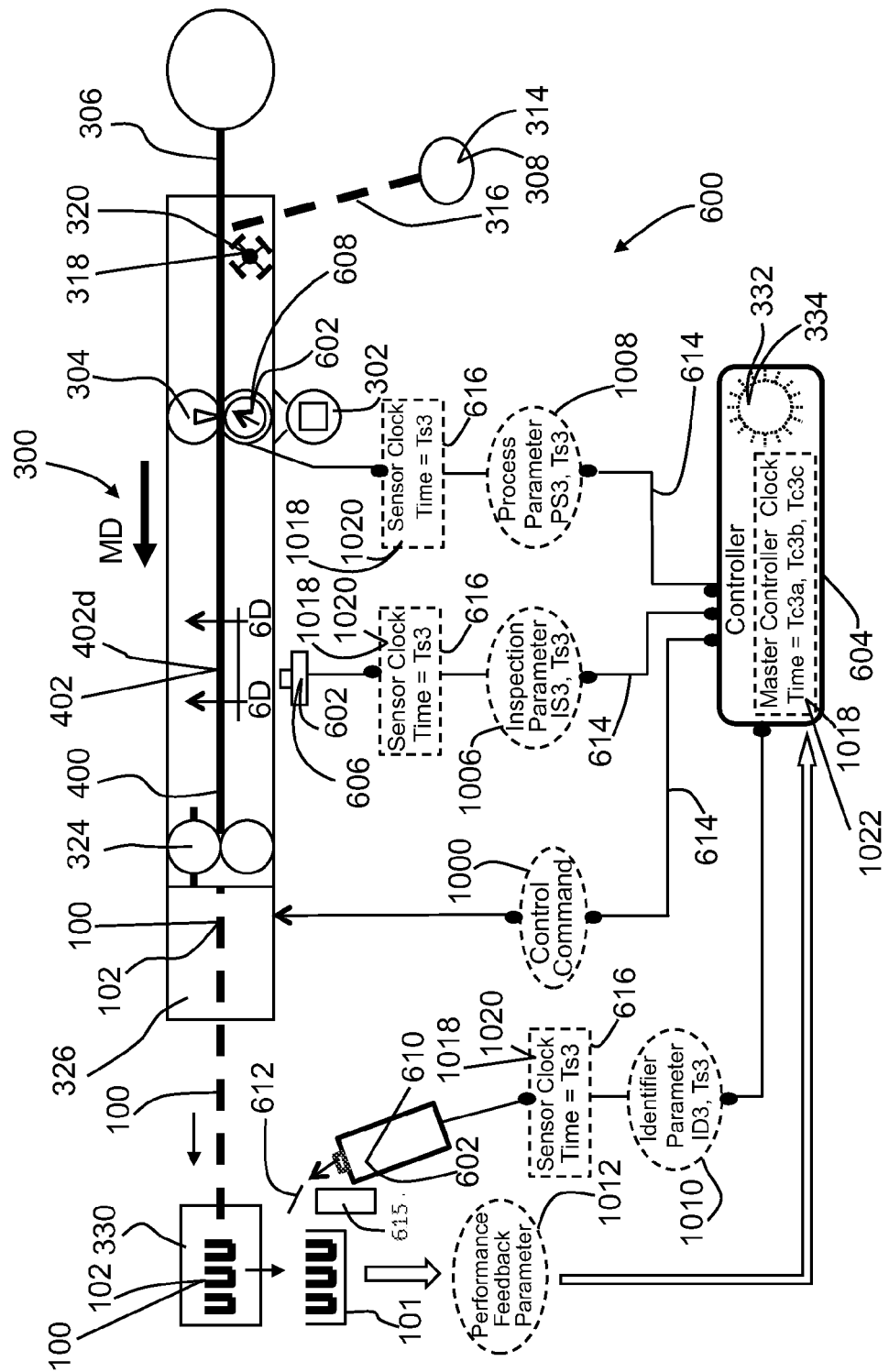
FIG. 5D is a schematic representation of an implementation of an absorbent article converting line and control system.

Next, FIGS. 5D and 6D show the continued advancement of the base substrate 306 in the machine direction MD, and in particular, advancement of a fourth virtual product 402d past the inspection sensor 606. FIG. 5D shows a third process parameter PS3 having a corresponding time stamp, Ts3a, being communicated to the communication network 614. PS3 may be configured to provide an indication of the applied pressure of the mechanical bonding unit 304 while creating the bonds 150 on the fourth virtual product 402d. Simultaneously, the time reported by master controller clock 1022 is Tc3a. A third inspection parameter, IS3, having a corresponding time-stamp, Ts3b, is also being communicated to the communication network 614. IS3 may be configured to provide an indication of the quality and presence of bonds 150 on the fourth virtual product 402d. In particular, IS3 may provide an indication of the absence and degraded quality of some bonds 150 on the first back ear 111a, represented by two missing discrete, black crescent shaped areas and the two discrete, gray crescent-shaped areas in FIG. 6D. Simultaneously, the time reported by master controller clock 1022 is Tc3b. In addition, a third identifier parameter, ID3, having a corresponding time-stamp, Ts3c, is being communicated to the communication network 614. ID3 may be configured to provide an indication of the unique identifier on the fourth virtual product 402d. Simultaneously, the time reported by master controller clock 1022 is Tc3c. Again, PS3, IS3, and ID3 may not be immediately received by the controller 604.

As previously mentioned, some amount of time may pass before the controller 604 receives the process parameters 1008, inspection parameters 1006, and identifier parameters 1010 from the communication network 614. Some such time delays may be the result of the non-deterministic nature of the Ethernet IP network. There may also be additional time before a controller analyzes the inspection parameters based on the controller's program cycle or loop time. However, notwithstanding such time delays, once the controller receives and analyzes process, inspection, and identifier parameters, the controller can use the corresponding time-stamps to correlate the process, inspection, and identifier parameters with particular virtual products 402. For example, the controller may receive and analyze PS3, IS3, and ID3 at some time after being provided to the communication network 614. However, along with PS3, IS3, and ID3, the controller 604 will receive Ts3a, Ts3b, and Ts3c, which were provided by the sensor clocks 1020. Because the sensor clocks 1020 are synchronized with the master controller clock 1022, the controller 604 can correlate PS3, IS3, and ID3 with the fourth virtual product 402d. Because the process parameters 1008, inspection parameters 1008, and identifier parameters 1010 have time-stamps provided from sensor clocks 1020 that are synchronized with the master controller clock 1022, the controller 604 can correlate the process parameters 1008, inspection parameters 1008, and identifier parameters 1010 with actual physical locations on the substrates and/or components advancing through the converting line 300 without having to account for various system time delays, such as time delays in the communication network and controller loop times. As such, the correlated location of the process parameters 1008, inspection parameters 1008, and identifier parameters 1010 on the substrates and/or components may be accurate to within the accuracy of the sensor clock with respect to the master controller clock. For example, where the clock accuracy meets the software implementation of IEE1588, the clocks may be assured to be accurate within 0.1 milliseconds. Expanding on the above discussion, it is to be appreciated that the controller 604 can utilized the machine axis 332 to further divide the virtual products 402 into virtual segments 404, such as described above with reference to FIG. 3. As such, the controller 604 may correlate the process parameters 1008, inspection parameters 1008, and identifier parameters 1010 with actual physical locations within the virtual products 402. In turn, the controller 604 correlates the virtual products 402 with individual products 102.

Expanding on the example implementation provided above with reference to FIGS. 5A-6D, the controller 604 may be adapted to send various types of control commands 1000 to the converting line 300, such as for example reject commands and/or shutdown commands. Such control commands 1000 may be based on process parameters 1008 and/or inspection parameters 1006. As described above with reference to FIG. 4, the controller 604 may include target inspection parameters 1014 and/or target process parameters 1016. During the manufacturing process, the controller 604 may compare inspection parameters 1008 to corresponding target inspection parameters 1014 to generate control commands 1000. Similarly, the controller 604 may compare process parameters 1008 to corresponding target process parameters 1016 to generate control commands 1000. For example, the controller 604 may have compared PS3 to target applied pressure of the mechanical bonding unit 304, and may have compared IS3 to a target quality and presence of bonds 150. If PS3 and IS3 were found to be within allowable limits based on the targets, the controller 604 may not have provided an alarm and/or issued reject and/or shutdown control commands 1000.

As described above, the controller may later receive performance feedback parameters 1012 that may include various types of information and/or data relating to the articles 102 produced by the converting line 300. And the performance feedback parameters 1012 can then be used as a basis to adjust target manufacturing parameters, such as the target inspection parameters 1014 and/or target process parameters 1016. For example, performance feedback parameters 1012 may provide an indication that the bonds 150 on products 102 corresponding with PS3 and IS3 may have an unacceptable failure rate, as for example, indicated by consumers providing the performance feedback parameters 1012. As such, the correlated performance feedback parameters 1012, correlated inspection parameters 1006, and correlated process parameters 1008 may be used to adjust target inspection parameters 1014 and/or target process parameters 1016. For example, in future manufacturing operations, the controller 604 will compare a process parameter of PS3 to the adjusted target applied pressure of the mechanical bonding unit 304, and will compare a inspection parameter of IS3 to the adjusted target quality and presence of bonds 150. As such, PS3 and IS3 may be found to be outside allowable limits based on the adjusted targets, and in turn, the controller 604 may provide an alarm and/or issue reject and/or shutdown control commands 1000.

Additionally, the performance feedback data, inspection parameters and process parameters may be formed into a process model for use in process troubleshooting or process or product improvement. In this example, unacceptable product performance may correlate to excessive values in the applied pressure of the mechanical bonding unit and may be indicated by certain values of an inspection parameter IS3. Modeling software may be used to monitor IS3 and PS3 in such a way as to alert the operator to an abnormal condition before the machine enters a state where product with unacceptable performance potential is produced.

Other examples of the implementation of the above system include utilizing the correlated data collected by the system to populate process and machinery models for use in process improvement. The correlations between product performance feedback 1012, whether from consumers or from quality laboratory testing to the process and inspection parameters 1002, 1006 can be used to provide analytical results when testing new raw materials, such as substrates, nonwoven or elastics as well as new designs for process machinery such as nip rolls, web guides or rotary knives. This may result in acceleration of the innovation process in that testing can be done more quickly.

Additionally, hitherto unknown causal relationships may be discovered and documented through using advanced mathematical techniques such as multivariate analyses and principal component analysis (PCA). Since the data is tightly correlated, determination of these relationships allows a high confidence in the mathematical models of the process and equipment, eliminating the need for physical testing and replacing it with mathematical modeling. The tight correlation of data and the normalization of time-stamps simplify the data mining process and increase the fidelity of autonomous data mining techniques. Traditionally, data must be conditioned and preprocessed to synchronize the reported time-stamps to the correlated product. Usually the preprocessing must be manually accomplished based on detailed process understanding or rely on cross correlation techniques that may indicate false causal relationships or obscure true causal relationships. The use of correlated data with normalized time-stamps increases the probability that a reported causal relationship is true and reduces the probability of falsely reporting a causal relationship.

Determination of causal relationships, either through direct correlation or through advanced mathematical modeling may also be used to enable real-time monitoring of process and inspection parameters. Such monitoring may be capable of tracking degradation trends in process and inspection parameters that indicate a trend towards unacceptable product performance. Thus the prognostic capability of the system may be used to either execute a control action or alert the line operator to take corrective action before the product enters a state where there would be unacceptable performance for the consumer.

It is to be appreciated that the methods and systems disclosed herein may be utilized to monitor the quality of substrates and components as well as respective placements during the manufacture of absorbent articles, such as for example, topsheets, backsheets, absorbent cores, ears, waist features, and graphics printed thereon. It is also to be appreciated that the systems and methods described herein may also be utilized in combination with other types of control systems and methods, such as described in U.S. Pat. Nos. 8,145,338; 8,145,344; and 8,145,343. Further, the methods and systems described herein may be utilized in other types of control systems and methods such as for example: data storage and correlation methods with repeat application devices and multiple application stations such as described in U.S. Pat. No. 6,829,516; raw material database integration such as described in U.S. Pat. No. 7,162,319; web guide control methods and systems such as described in U.S. Pat. No. 6,801,828; and data mining and trending methods and systems such as described in U.S. Pat. No. 6,845,278.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacture of absorbent products, the method comprising the steps of:

providing a communication network;

connecting a first sensor with the communication network;
connecting a second sensor with the communication network;
connecting a controller with the communication network;
advancing a substrate in a machine direction through a converting apparatus;
virtually segmenting the substrate into a plurality of virtual products along the machine direction;
sequentially adding component parts to the substrate;
inspecting the substrate and component parts with the first sensor;
communicating inspection parameters from the first sensor to the controller;
comparing the inspection parameters with a target inspection parameter;
inspecting a process with the second sensor;
communicating process parameters from the second sensor to the controller;
comparing the process parameters with a target process parameter;
cutting the substrate with component parts added thereto into discrete absorbent articles;
packaging the discrete absorbent articles;
receiving performance feedback parameters based on the packaged absorbent articles;
correlating at least one inspection parameter with a selected packaged absorbent article;
correlating at least one process parameter with the selected packaged absorbent article;
correlating at least one performance feedback parameter with the selected packaged absorbent article; and
adjusting at least one target inspection parameter or at least one the target process parameter based on the performance feedback parameter.

2. The method of claim 1, wherein the absorbent articles are diapers.

3. The method of claim 2, wherein the components are back ears.

4. The method of claim 3, further comprising the step of bonding the back ear to the substrate with a mechanical bonding unit, and wherein one process parameter corresponds with an applied pressure of the mechanical bonding unit.

5. The method of claim 4, wherein the at least one target process parameter corresponds with a target applied pressure of the mechanical bonding unit.

6. The method of claim 3, wherein the at least one target inspection parameter corresponds with a target placement of the back ears on the substrate.

7. The method of claim 3, wherein at least one of the performance feedback parameter corresponds with separation of back ears from diapers while under tension.

8. The method of claim 1, further comprising the step of compiling correlated feedback parameters, correlated inspection parameters, and correlated process parameters to create, modify, or validate manufacturing process models.

9. The method of claim 1, further comprising the step of compiling correlated feedback parameters, correlated inspection parameters, and correlated process parameters to create, modify, or validate product models.

10. The method of claim 1, wherein the step of receiving performance feedback parameters based on the packaged absorbent articles further comprises soliciting and recording consumer feedback relating to in use performance of the packaged absorbent articles.

11. The method of claim 10, further comprising the step of compiling correlated feedback parameters, correlated inspection parameters, and correlated process parameters to harmonize quality specification limits with consumer feedback.

12. The method of claim 1, wherein one inspection parameter corresponds to a detected missing component on the substrate.

13. The method of claim 1, wherein one inspection parameter corresponds to measured placement of a component on the substrate.

14. The method of claim 1, wherein the performance feedback parameter is selected from the group consisting of: leakage; component alignment; and absorbent article fit.

15. The method of claim 1, further comprising the step of testing the selected packaged absorbent article.

16. A method for manufacture of absorbent products, the method comprising the steps of:
providing a communication network;
connecting a first sensor with the communication network;
connecting a second sensor with the communication network;
connecting a controller with the communication network;
advancing a substrate in a machine direction through a converting apparatus at a first speed;
virtually segmenting the substrate into a plurality of virtual products along the machine direction;
virtually dividing the virtual products into a plurality of virtual segments along the machine direction;
sequentially adding component parts to the substrate;
inspecting the substrate and component parts with the first sensor;
communicating inspection parameters from the first sensor to the controller;
comparing the inspection parameters with a target inspection parameter;
inspecting a process with the second sensor;
communicating process parameters from the second sensor to the controller;
comparing the process parameters with a target process parameter;
cutting the substrate with component parts added thereto into discrete absorbent articles;
packaging the discrete absorbent articles;
receiving performance feedback parameters based on the packaged absorbent articles;
correlating at least one inspection parameter with a selected packaged absorbent article;
correlating at least one process parameter with the selected packaged absorbent article;
correlating at least one performance feedback parameter with the selected packaged absorbent article; and
adjusting at least one target inspection parameter or at least one the target process parameter based on the performance feedback parameter.

17. The method of claim 16, wherein the first and second sensors each include a sensor clock, wherein the controller includes a controller clock; and further comprising the step of:
synchronizing the sensor clocks with the controller clock such that reported times of the controller clock and the sensor clocks can be correlated;
assigning a time-stamp to each inspection parameter, each time-stamp based on the sensor clock;

receiving the inspection parameters and corresponding time-stamps from the communication network into the controller; and correlating each inspection parameter with one virtual segment based on the time-stamp of the inspection parameter and the first speed of the substrate.

18. The method of claim 16, further comprising the step of compiling correlated feedback parameters, correlated inspection parameters, and correlated process parameters to create, modify, or validate prognostic systems.

19. The method of claim 16, further comprising the step of compiling correlated feedback parameters, correlated inspection parameters, and correlated process parameters to facilitate autonomous data mining.

20. A method for manufacture of absorbent products, the method comprising the steps of:

providing a communication network;
connecting a first sensor with the communication network;
connecting a second sensor with the communication network;
connecting a controller with the communication network;
advancing a substrate in a machine direction through a converting apparatus;
virtually segmenting the substrate into a plurality of virtual products along the machine direction;
virtually dividing the virtual products into a plurality of virtual segments along the machine direction;
sequentially adding component parts to the substrate;
inspecting the substrate and component parts with the first sensor;
communicating inspection parameters and time-stamps from the first sensor to the controller;
inspecting a process with the second sensor;
communicating process parameters and time-stamps from the second sensor to the controller;
normalizing time-stamps for inspection parameters to a reference location or product;
normalizing time-stamps for process parameters to a reference location or product;
cutting the substrate with component parts added thereto into discrete absorbent articles;
packaging the discrete absorbent articles;
receiving performance feedback parameters based on the packaged absorbent articles;
determining and normalizing time-stamps for performance feedback parameters to a reference location or product;
correlating at least one inspection parameter with a selected packaged absorbent article;
correlating at least one process parameter with the selected packaged absorbent article;
correlating at least one performance feedback parameter with the selected packaged absorbent article; and
storing inspection parameters, process parameters, and product performance parameters in a historian.

* * * * *